United States Patent
Yamahana et al.

(10) Patent No.: US 10,140,701 B2
(45) Date of Patent: Nov. 27, 2018

(54) X-RAY COMPUTED TOMOGRAPHY APPARATUS AND INFORMATION PROCESSING APPARATUS

(71) Applicant: TOSHIBA MEDICAL SYSTEMS CORPORATION, Otawara-Shi (JP)

(72) Inventors: Masao Yamahana, Nasushiobara (JP); Shinya Kawanabe, Otawara (JP); Takahiro Yoda, Nasushiobara (JP); Risa Onishi, Nasushiobara (JP); Hiroyuki Onuki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 202 days.

(21) Appl. No.: 14/670,649

(22) Filed: Mar. 27, 2015

(65) Prior Publication Data

US 2015/0199813 A1 Jul. 16, 2015

Related U.S. Application Data

(63) Continuation of application No. PCT/JP2013/081060, filed on Nov. 18, 2013.

(30) Foreign Application Priority Data

Nov. 16, 2012 (JP) ................................ 2012-252046
Nov. 18, 2013 (JP) ................................ 2013-237895

(51) Int. Cl.
*A61B 6/00* (2006.01)
*G06T 7/00* (2017.01)
*A61B 6/03* (2006.01)

(52) U.S. Cl.
CPC ............ *G06T 7/0012* (2013.01); *A61B 6/032* (2013.01); *A61B 6/5258* (2013.01); *A61B 6/586* (2013.01);
(Continued)

(58) Field of Classification Search
CPC ..... A61B 6/032; A61B 6/5205; A61B 6/5258; A61B 6/5264; A61B 6/563; A61B 6/586;
(Continued)

(56) References Cited

U.S. PATENT DOCUMENTS

| | | | | |
|---|---|---|---|---|
| 5,434,900 A | * | 7/1995 | Tanaka ..................... | A61B 6/56 378/15 |
| 5,740,222 A | * | 4/1998 | Fujita ..................... | A61B 6/032 378/4 |

(Continued)

FOREIGN PATENT DOCUMENTS

| | | |
|---|---|---|
| JP | 2001-170042 A | 6/2001 |
| JP | 2002-277993 A | 9/2002 |

(Continued)

OTHER PUBLICATIONS

International Search Report dated Feb. 10, 2014 for PCT/JP2013/081060 Filed on Nov. 18, 2013 (English Language).

(Continued)

*Primary Examiner* — Irakli Kiknadze
(74) *Attorney, Agent, or Firm* — Oblon, McClelland, Maier & Neustadt, L.L.P.

(57) ABSTRACT

A reconstruction unit (a pre-processor, a reconstruction unit and an image processor) generates a reconstruction image based on output from the X-ray detector. A correction parameter storage stores correction parameters in time series, the correction parameters being used for correction by which noise or artifact is reduced in processing performed by the reconstruction image unit. A correction parameter analysis unit determines whether or not an abnormal condition occurs based on a temporal change in the correction parameters stored in the correction parameter storage. A notification unit issues a notification indicating the occurrence of an abnormal condition where the correc- (Continued)

tion parameter analysis unit determines that the abnormal state has occurred.

14 Claims, 5 Drawing Sheets

(52) U.S. Cl.
CPC ........... *A61B 6/5205* (2013.01); *A61B 6/5264* (2013.01); *A61B 6/563* (2013.01); *G06T 2207/10004* (2013.01); *G06T 2207/10081* (2013.01)

(58) Field of Classification Search
CPC ......... A61B 6/581; A61B 6/505; A61B 6/583; A61B 6/4423; A61B 6/508; A61B 6/4509; A61B 6/482; A61B 8/0875; A61B 2576/02; A61B 5/002; A61B 5/0022; A61B 5/4504; A61B 5/4547; A61B 5/7264; A61B 5/748; A61B 6/14; A61B 6/469; A61B 5/055; A61B 5/743; A61B 6/461; A61B 6/463; A61B 6/50; A61B 6/582; A61B 6/584; G06T 2207/10004; G06T 2207/10081; G06T 7/0012; G06F 19/3406; G06F 19/3412; G06F 19/345; G06Q 50/22; G06N 5/04; A61K 2300/00; A61K 33/06; A61K 33/14; A61K 31/198; A61K 31/704; A61K 45/06; A61K 9/0075; A61K 31/439; A61K 31/661; A61K 31/6615; A61K 38/00; A61K 47/183; A61K 31/506; A61K 31/58; A61K 38/14; A61K 2039/505; A61K 38/12; G01T 1/2985; G01D 5/145

USPC ...................................... 378/4, 8, 15, 19, 117
See application file for complete search history.

(56) References Cited

U.S. PATENT DOCUMENTS

| | | | |
|---|---|---|---|
| 7,440,547 B2* | 10/2008 | Ishiyama | A61B 6/032 378/101 |
| 7,634,308 B2* | 12/2009 | Ogawa | A61B 6/481 378/196 |
| 2003/0076920 A1* | 4/2003 | Shinno | A61B 6/032 378/4 |
| 2003/0103595 A1* | 6/2003 | Raupach | G06T 11/005 378/4 |
| 2003/0156683 A1 | 8/2003 | Adachi | |
| 2004/0138920 A1 | 7/2004 | Sawanaga et al. | |
| 2006/0149598 A1 | 7/2006 | Adachi | |
| 2011/0049343 A1 | 3/2011 | Yamaguchi | |
| 2012/0093280 A1* | 4/2012 | Konno | A61B 6/032 378/7 |

FOREIGN PATENT DOCUMENTS

| | | |
|---|---|---|
| JP | 2002-277994 A | 9/2002 |
| JP | 2003-235836 A | 8/2003 |
| JP | 2004-357762 A | 12/2004 |
| JP | 2005-110794 A | 4/2005 |
| JP | 2009-219691 A | 10/2009 |
| JP | 2011-50472 A | 3/2011 |
| WO | WO 2009/113418 A1 | 9/2009 |

OTHER PUBLICATIONS

International Written Opinion dated Feb. 10, 2014 for PCT/JP2013/081060 Filed on Nov. 18, 2013.

* cited by examiner

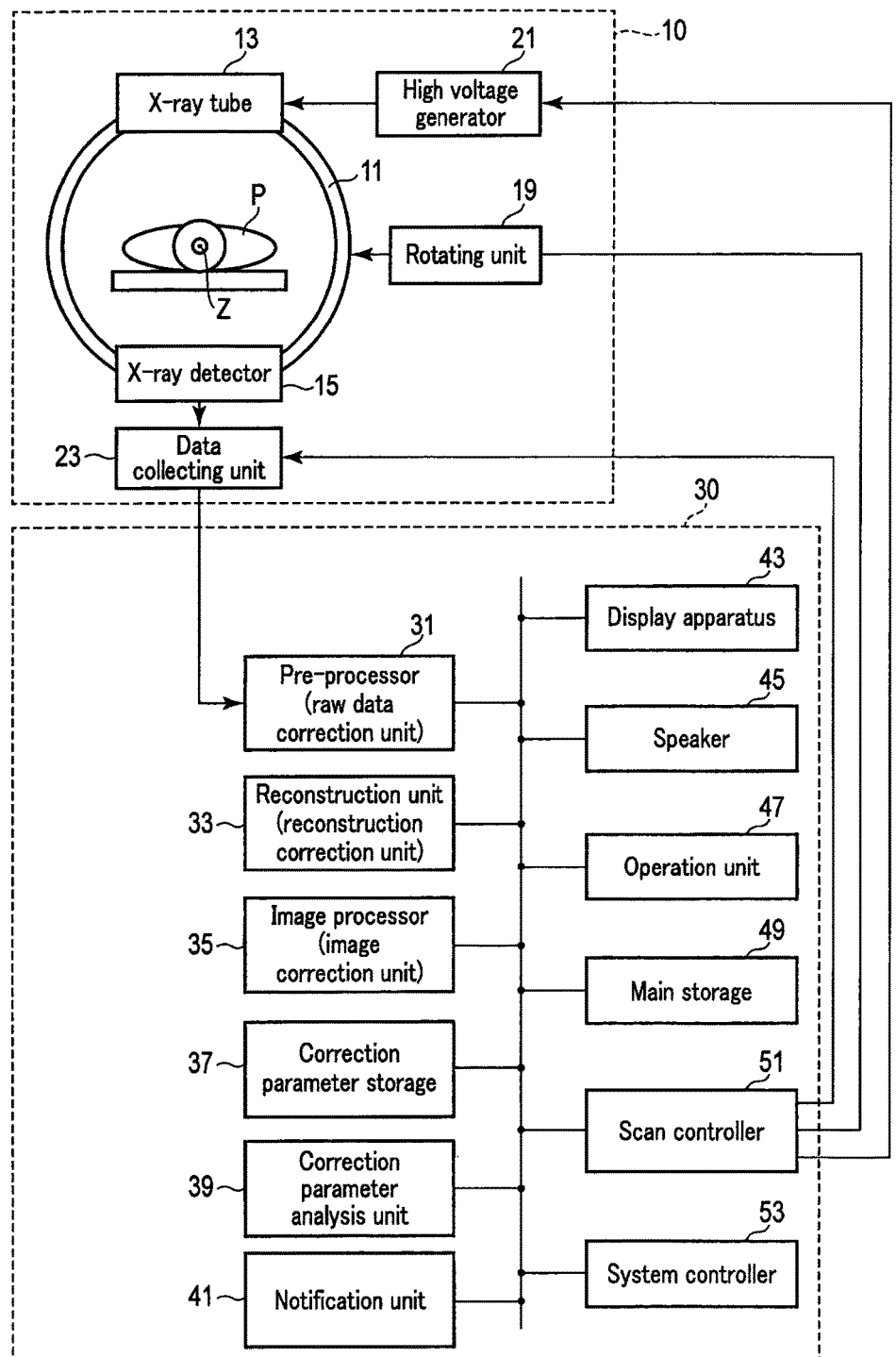
F I G. 1

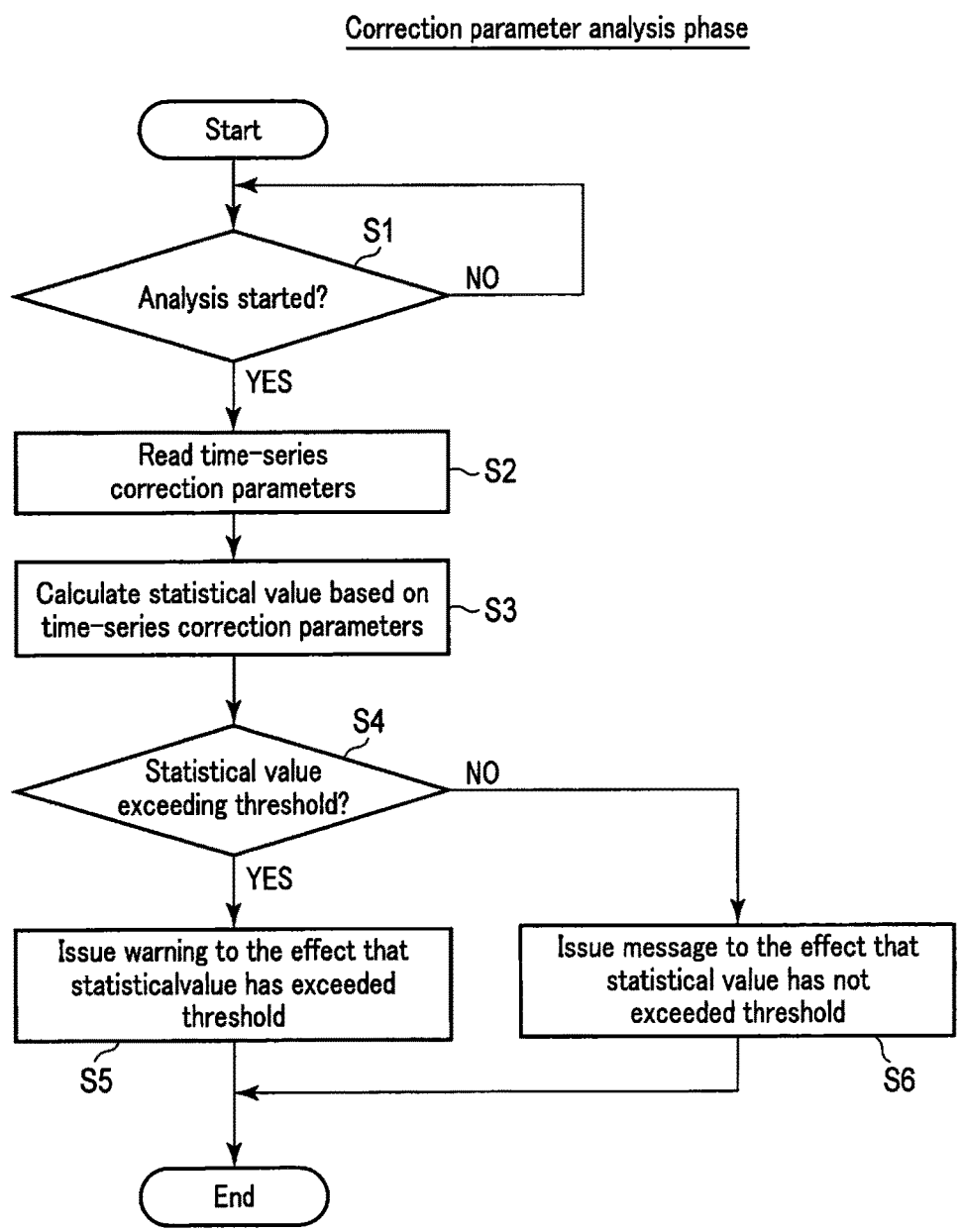
F I G. 3

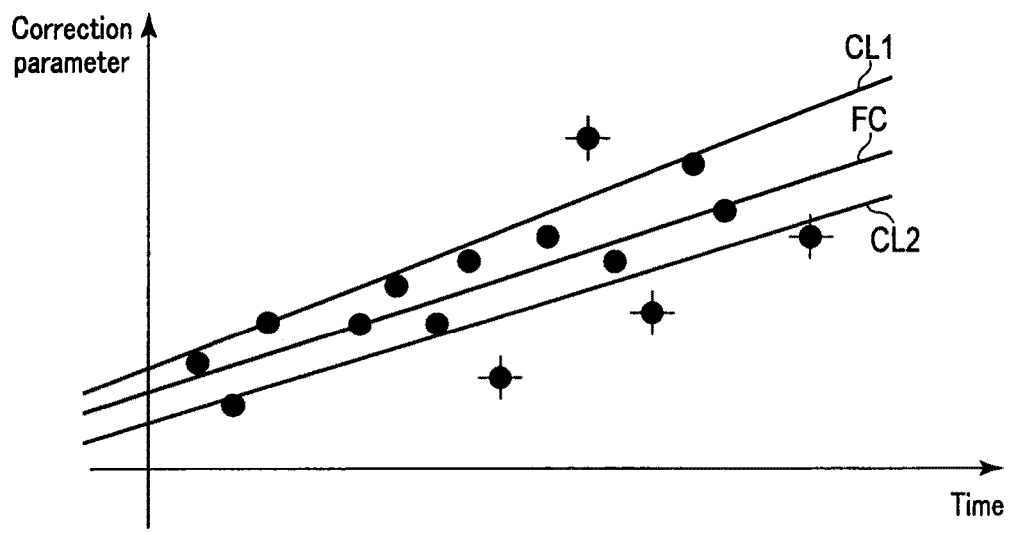
F I G. 4

X-RAY COMPUTED TOMOGRAPHY APPARATUS AND INFORMATION PROCESSING APPARATUS

CROSS-REFERENCE TO RELATED APPLICATIONS

This application is a Continuation Application of PCT Application No. PCT/JP2013/081060, filed Nov. 18, 2013 and based upon and claims the benefit of priority from the Japanese Patent Application No. 2012-252046, filed Nov. 16, 2012, and the Japanese Patent Application No.2013-237895, filed Nov. 18, 2013, the entire contents of all of which are incorporated herein by reference.

FIELD

Embodiments described herein relate generally to an X-ray computed tomography apparatus and an information processing apparatus.

BACKGROUND

An abnormal state of an X-ray computed tomography apparatus is detected. The abnormal state of the X-ray computed tomography apparatus can be confirmed by checking an error log or observing a reconstruction image. In this case, a change in the state of the apparatus cannot be noticed until the apparatus becomes abnormal. An abnormal state can be detected by performing a CT scan of a phantom for image quality analysis at the time of a routine check of the apparatus. To be more specific, a service technician checks an output of the X-ray detector or a reconstruction image, or automatic analysis is performed using analysis software. In this case, the state of the apparatus cannot be confirmed until a regular check is actually performed.

BRIEF DESCRIPTION OF THE DRAWING

FIG. 1 shows an X-ray computed tomography apparatus according to the present embodiment.

FIG. 3 is a flowchart illustrating a typical flow by which the correction parameters are analyzed under the control of the system controller shown in FIG. 1.

FIG. 4 is a graph showing how the correction parameters change with time, the graph illustrating both a statistical value calculation process in Step S3 of FIG. 3 and a determination process in Step S4 of the same Figure.

DETAILED DESCRIPTION

Figure 2:
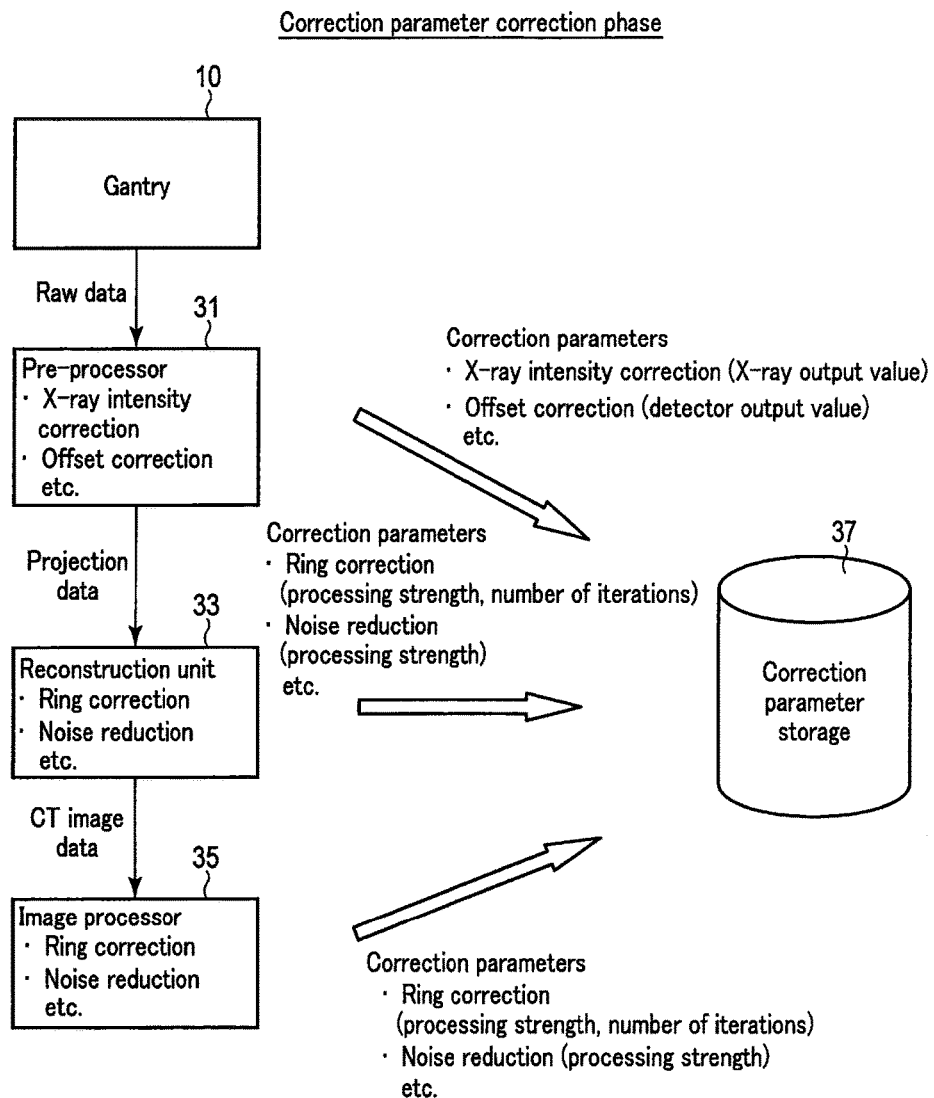
FIG. 2 is an explanatory diagram showing how correction parameters are collected in the X-ray computed tomography apparatus of the embodiment.

In general, according to one embodiment, an X-ray computed tomography apparatus includes an X-ray tube, an X-ray detector, a reconstruction unit, a storage, a determination unit, and a notification unit. The X-ray tube generates X-rays. The X-ray detector detects X-rays generated from the X-ray tube. The reconstruction unit generates a reconstruction image based on output data in accordance with an electric signal from the X-ray detector. The storage stores correction parameters in time series.

The correction parameters are used for correction by which noise or artifact is reduced in processing performed by the reconstruction unit. The determination unit determines whether the apparatus is in an abnormal state based on a temporal change in the correction parameters stored in the storage. The notification unit issues a notification of occurrence of an abnormal condition when the determination unit determines that the apparatus is in the abnormal state.

An X-ray computed tomography apparatus and an information processing apparatus according to the present embodiment will now be described with reference to the accompanying drawings.

FIG. 1 shows an X-ray computed tomography apparatus according to the present embodiment. As shown in FIG. 1, the X-ray computed tomography apparatus of the embodiment includes a gantry 10 and a console 30. The gantry 10 is installed in a CT photography room of a hospital or the like. The console 30 is installed in the CT photography room or in a control room adjacent to the CT photography room. The console 30 controls the gantry 10 based on the instructions by the operator.

The gantry 10 is provided with a rotating frame 11 inside the opening of a housing (not shown). The rotating frame 11 is received in the housing in such a manner that the central axis Z of the housing and the central axis Z (the axis of rotation) of the rotating frame are coincident. The rotating frame 11 is provided with an X-ray tube 13 and an X-ray detector 15 facing each other. The rotating frame supports the X-ray tube 13 and the X-ray detector 15 in such a manner that they are rotatable around the axis Z of rotation. A field of view is defined within the housing or in the opening of the rotating frame 11. A top plate 17 is positioned in such a manner that the imaging region of a subject (patient) P is located in the FOV. The rotating frame 11 is connected to a rotating unit 19. The rotating unit 19 rotates the rotating frame 11 at a constant angular speed under the control of a scan controller 51 inside the console 30, thereby rotating the X-ray tube 13 and the X-ray detector 15 about the axis Z of rotation.

Applied with a high voltage and supplied with a filament current from a high voltage generator 21, the X-ray tube 13 generates X-rays. The high voltage generator 21 applies to the X-ray tube 13 a high voltage controlled by the scan controller 51, and supplies a filament current to the X-ray tube 13.

The X-ray detector 15 detects X-rays generated by the X-ray tube 13 and passing through the subject P. The X-ray detector 15 is provided with a plurality of X-ray detection elements arranged in two dimensions. For example, the X-ray detection elements are arranged along an arc whose center coincides with the axis Z of rotation. The direction in which the X-ray detection elements are arranged along the arc is referred to as a channel direction. The X-ray detection elements arranged in the channel direction are referred to as X-ray detection element arrays. The X-ray detection element arrays are arranged in the direction along the axis Z of rotation. Each X-ray detection element detects an X-ray generated by the X-ray tube 13, and generates an electric signal (a current signal) proportional to the intensity of the detected X-ray. The generated electric signal is supplied to a data collecting unit 23.

Under the control of the scan controller 51, the data collecting unit 23 collects raw data in accordance with electric signals, using the X-ray detector 15. To be more specific, the data collecting unit 23 generates an integral signal for each view based on an analog electric signal supplied from the X-ray detector 15, and subjecting the integral signal to A/D conversion, thereby generating digital data. This digital data is referred as raw data. As is well known, a view corresponds to a rotating angle of the rotating frame 11 around the axis Z of rotation. In terms of the signal processing, a view corresponds to a sampling point at which data is acquired when the rotating frame 11 rotates. The raw data is supplied to the console 30 by way of a non-contact data transmitter (not shown) provided inside the gantry 10.

The console 30 comprises a pre-processor 31, a reconstruction unit 33, an image processor 35, a correction parameter storage 37, a correction parameter analysis unit 39, a notification unit 41, a display apparatus 43, a speaker 45, an operation unit 47, a main storage 49, a scan controller 51 and a system controller 53. The pre-processor 31, reconstruction unit 33 and the image processor 35 jointly form a reconstruction unit.

The pre-processor 31 generates projection data by subjecting the raw data from the gantry 10 to pre-processing, such as logarithmic conversion. The pre-processing includes various types of correction processing for raw data, in addition to the logarithmic conversion mentioned above. In other words, the pre-processor 31 functions as a raw data correction unit as well. The projection data is stored in the main storage 49 for each view.

The reconstruction unit 33 generates reconstruction image data representing how the CT values in an imaging area are spatially distributed based on the projection data (the reconstruction image data will be hereinafter referred to as "CT image data"). As an image reconstruction algorithm, it is possible to use an existing image reconstruction algorithm such as an analytical image reconstruction method, e.g., an FBP (Filtered Back Projection) method, or a statistical image reconstruction method, e.g., an ML-EM (Maximum Likelihood Expectation Maximum) method or OS-EM (Ordered Subset Expectation Maximization) method, or another known image reconstruction algorithm may be used. Each of these image reconstruction algorithms incorporates various types of correction processing for projection data. As can be seen from this, the reconstruction unit 33 functions as a reconstruction correction unit as well. The CT images are stored in the main storage 49.

The image processor 35 performs various types of image processing for CT image data. The image processing includes three-dimensional image processing, image correction processing, etc. The three-dimensional image processing includes, for example, volume rendering, surface rendering, pixel value projection processing, multi-planar reconstruction (MPR), etc. Typically, maximum intensity projection (MIP) is used as the pixel value projection processing. By executing the three-dimensional image processing, a two-dimensional display image is generated from the CT image data. The image correction processing includes various types of correction processing performed for the CT image data. As can be seen from this, the image processor 35 functions as an image correction unit as well.

The correction parameter storage 37 stores, in time series, correction parameters used in the correction processing performed by the pre-processor 31, reconstruction unit 33 and image processor 35. The correction parameters includes (i) correction values (correction strength) directly applied to real data such as raw data, projection data and CT image data, and (ii) measurement values used for calculating correction values. The correction parameters may include a parameter representing the number of times the correction processing is repeated. The correction parameters are generated by the pre-processor 31, the reconstruction unit 33 or the image processor 35 in accordance with the types of correction processing. The correction parameters are stored in association with the times when they are generated.

The correction parameter analysis unit 39 determines whether or not the statistical values of the correction parameters stored in the correction parameter storage 37 in time series exceed predetermined thresholds. A statistical indicator for evaluating the temporal variations in the correction parameters is applied as the statistical value mentioned above.

The notification unit 41 sends out an operating condition of the X-ray computed tomography apparatus 1 diagnosed by the correction parameter analysis unit 39. Specifically, the notification unit 41 issues a warning if the correction parameter analysis unit 39 determines that a statistical value exceeds a threshold. The notification unit issues a warning indicating the occurrence of an abnormal condition by use of the display apparatus 43 or speaker 45. If the correction parameter analysis unit 39 determines that the statistical value does not exceed the threshold, then the notification unit 41 sends out a message to that effect by use of the display apparatus 43 or speaker 45.

Where the correction parameter analysis unit 39 determines that the statistical value exceeds the threshold, the display apparatus 43 displays a warning message on a display in accordance with the instructions sent from the notification unit 41. Where the correction parameter analysis unit 39 determines that the statistical value does not exceed the threshold, the display apparatus 43 displays a message to that effect on the display in accordance with the instructions sent from the notification unit 41. The display may be a CRT display, a liquid crystal display, an organic EL display, a plasma display, or any other type of display. The display apparatus 43 can show display images and various types of information which are shown in an ordinary CT examination, such as a scan plan window.

Where the correction parameter analysis unit 39 determines that the statistical value exceeds the threshold, the speaker 45 issues a voice message or a warning sound in accordance with the instructions sent from the notification unit 41. Where the correction parameter analysis unit 39 determines that the statistical value does not exceed the threshold, the speaker 45 issues a voice message to that effect or a notification sound in accordance with the instructions sent from the notification unit 41.

The operation unit 47 is supplied with various types of instructions and information which the user enters from an input device. The input device may be a keyboard, a mouse, or various types of switches.

The main storage 49 is a main memory configured to store various types of information. For example, the main storage 49 stores projection data, CT image data, and data on display images.

The scan controller 51 controls the rotating unit 19, the high voltage generator 21 and the data collecting unit 23 in such a manner that a CT scan is executed in accordance with a scan plan.

The system controller 53 functions as a major controller of the X-ray computed tomography apparatus 1. The system controller 53 reads an operation condition diagnosis program according to the present embodiment out of the main storage 49 and controls the structural elements of the apparatus in accordance with the read program. As a result, the operation state diagnosis processing according to the present embodiment is carried out.

A description will now be given of an operation of the X-ray computed tomography apparatus of the present embodiment. The operation condition diagnosis processing of the present embodiment includes two phases: correction parameter collection and correction parameter analysis. First, the collection parameter collection will be described.

FIG. 2 illustrates the correction parameter collection performed by the X-ray computed tomography apparatus of the present embodiment. The correction parameter collection is automatically performed for each CT scan.

As shown in FIG. 2, the gantry 10 collects digital raw data on the outputs of the X-ray detector in the CT scan. The pre-processor 31 subjects the raw data to pre-processing, thereby generating projection data. At this time, the pre-processor 31 executes correction processing for the raw data. The correction processing performed by the pre-processor 31 includes correction of the raw data in the normal X-ray CT, such as X-ray intensity correction and offset correction.

The X-ray intensity correction is performed for reducing the adverse effects which the variations in the intensity of the X-rays generated by the X-ray tube, namely the variations in the output, may have on the raw data. The X-rays undergo temporal variations, due to temporal variations in the tube voltage and temporal variations in the tube current. The temporal variations in X-ray intensity cause artifact in the CT image data. The X-ray intensity correction is performed using a correction parameter such as an X-ray output value. The X-ray output value is detected by a reference detector, which is provided separately from the X-ray detector 15. The reference detector is so located that no object is interposed between the reference detector and the X-ray tube 13 and detects X-rays which are generated by the X-ray tube 13 and do not pass through any object. The X-ray output value is measured by the reference detector before or during a CT scan. The measured X-ray output value is stored in the correction parameter storage 37 in association with the measurement time. The pre-processor 31 corrects the raw data, using the X-ray output value detected by the reference detector. The correction parameter related to the X-ray intensity correction is not limited to the X-ray output value detected by the reference detector; it may be a tube voltage value or tube current value measured by the high voltage generator 21, for example.

The correction parameter related to the X-ray intensity correction is not limited to the X-ray output value detected by the reference detector, the tube voltage value or the tube current value, and may be any parameter used in the X-ray intensity correction.

The offset correction is performed for reducing the adverse effects which the variations in the input/output characteristics of the X-ray detection elements of the X-ray detector 15, namely the variations in the output, may have on the raw data. Even if the X-ray detection elements are produced based on the same product specifications, they may be different in shape or made of a non-uniform material. In addition, the environment in which they are used may not be constantly the same. For this reason, they do not necessarily have the same input/output characteristic under the same condition. Furthermore, a malfunctioning X-ray detection element may have a different input/output characteristic from that of a normally-functioning X-ray detection element. The variations in the input/output characteristics of the X-ray detection elements cause artifact in the CT image data. For the offset correction, the output value of each of the X-ray detection elements of the X-ray detector 15 (the output value will be hereinafter referred to as a "detector output value" is used as a corrector parameter. Typically, the detector output value of each X-ray detection element is measured before a CT scan. The detector output value is stored in the correction parameter storage 37 in association with its measurement time. The pre-processor 31 corrects raw data based on the detector output values of the multiple X-ray detection elements. For example, the pre-processor 31 determines a gain value for each of the X-ray detection elements based on the detector output values of the multiple X-ray detection elements, so that the detector output value of each X-ray detection element becomes uniform under the same condition. The gain value, determined in this manner, is applied to the detector output value of each X-ray detection element. The gain value may be used as a correction parameter. In this case, the gain value is stored in the correction parameter storage 37 in association with both an X-ray detection element number and a calculation time.

The correction parameter related to the offset correction is not limited to the detection output value of each X-ray detection element or the gain value; it may be any parameter applicable to the offset correction.

Although the X-ray intensity correction and the offset correction were described above as specific examples of the correction processing performed by the pre-processor, the correction processing is not limited to these. For example, the correction processing performed by the pre-processor 31 may be beam hardening correction or body motion correction, and the correction parameter may be a correction parameter for beam hardening correction or a correction parameter for body motion correction.

As shown in FIG. 2, the reconstruction unit 33 generates CT image data by subjecting projection data to reconstruction processing. The reconstruction processing incorporates correction processing of the projection data. The correction processing performed by the reconstruction unit 33 includes ring correction and noise reduction processing, for example.

The ring correction is performed for reducing data components that cause ring-shaped artifact (the data components will be hereinafter referred to as "ring components"). As a correction parameter related to the ring correction, the processing strength of ring correction or the number of iterations is used. The processing strength is, for example, a coefficient of a function for reducing ring components. The number of iterations represents the number of times the ring correction is repeatedly executed. The reconstruction unit 33 adjusts the processing strength or the number of iterations based on projection data. The user can adjust the processing strength or the number of iterations, using the operation unit 47. The processing strength and the number of iterations are stored in the correction parameter storage 37 in association with the measurement times.

The noise reduction processing is performed for reducing noise components. To be more specific, the noise reduction processing is smoothing processing for reducing noise components included in projection data. Smoothing strength is used as a correction parameter related to the noise reduction processing. The processing strength is stored in the correction parameter storage 37 in association with the measurement time.

As shown in FIG. 2, the image processor 35 subjects CT image data to image correction processing. The image correction processing, which the image processor performs for the CT image data, includes ring correction, noise reducing processing, etc. The ring correction and noise reduction processing performed by the image processor 35 are similar to the ring correction and noise reduction processing performed by the image reconstruction unit 33, except for the type of data to be corrected and processed. That is, the ring correction and noise reduction processing by the image processor 35 is executed for the CT image data, and the ring correction and noise reduction processing by the image processor 35 is executed for the projection data. In other words, the image processor 35 generates CT image data (reconstruction images) subjected to the image correction processing.

As described above, in the correction parameter collecting phase, the correction parameter storage 37 receives various correction parameters from the pre-processor 31, reconstruction unit 33 and image processor 35 and stores them. Each time the correction parameters are calculated or measured, they are stored in the correction parameter storage 37 in association with the times when they are generated. In this manner, the correction parameter storage 37 stores the correction parameters in time series.

The processing in the collection parameter collection aspect is performed as described above.

Next, a description will be given of the correction parameter analysis phase.

FIG. 3 is a flowchart illustrating a typical process for the correction parameter analysis performed under the control of the system controller 53.

As shown in FIG. 3, the system controller 53 is on standby and waits for an instruction for analysis of a correction parameter (Step S1). When the user wants to know the operating condition of the X-ray computed tomography apparatus of the present embodiment, the user enters an analysis start instruction by operating the operation unit 47. The correction parameters are analyzed not necessarily by a service technician; they can be analyzed by medical staff, including a doctor and a medical engineer. That is, the analysis start may be instructed either by the service technician or by the medical staff.

When the user operates the operation unit 47 and instructs the analysis start (YES in Step S1), the system controller 53 causes the correction parameter analysis unit 39 to perform read processing (Step S2). In Step S2, the correction parameter analysis unit 39 reads time-series correction parameters to be analyzed, from the correction parameter storage 37.

The types of correction parameters to be analyzed can be arbitrarily selected by use of the operation unit 47. As parameters to be analyzed, only one type may be selected, or two or more types may be selected.

After Step S2, the system controller 53 causes the correction parameter analysis unit 39 to perform calculation (Step S3). In Step 3, the correction parameter analysis unit 39 calculates a statistical value based on the read time-series correction parameters. The statistical value is used for evaluating the dynamic statistics of the time-series correction parameters. Typically, one statistical value is calculated based on the correction parameters of one type. For example, statistical values include an average, a change in the average, a standard deviation, a change in the standard deviation, a dispersion, a change in the dispersion, a standard distribution, a change in the standard distribution, the number of exception points, and a change in the number of exception points. One statistical value may be calculated based on the correction parameters of two or more types.

After Step S3, the system controller 53 causes the correction parameter analysis unit 39 to perform determination processing (Step 4). In Step S4, the correction parameter analysis unit 39 determines whether or not the statistical value calculated in Step S3 exceeds a threshold. This threshold is determined beforehand based on a combination of the type of correction parameters and the type of a statistical value. The threshold may be calculated based on the past correction parameters regarding the normal operating condition. Alternatively, the threshold may be an arbitrary value which the user enters from the operation unit 47. A deteriorated member or component of the X-ray computed tomography apparatus can be located in accordance with the type of a correction parameter and the type of a statistical value.

The statistical value calculation processing in Step S3 and the determination processing in Step S4 will be described with reference to FIG. 4, with the number of times by which ring correction is performed being mentioned as a specific example of a correction parameter. FIG. 4 is a graph in which correction parameters are plotted. In the graph of FIG. 4, the axis of ordinates represents a correction parameter (i.e., the number of times ring correction is repeated) and the axis of abscissa represents time. In FIG. 4, the black points are sampling points of correction parameters, the cross points are exceptional sampling points of correction parameters, the solid line is a fitting curve FC and standard distribution lines CL1 and CL2.

In Step S3, the correction parameter analysis unit 39 plots the read time-series correction parameters in the graph of FIG. 4. The correction parameter analysis unit 39 calculates fitting curve FC, standard distribution line CL1 and standard distribution line CL2 based on the sampling points of the time-series correction parameters. The fitting curve is a time-change curve representing an average motion value of a correction parameter at each point of time. Standard distribution line CL1 is a curve which is shifted in the plus direction from fitting curve FC by the standard deviation, while standard distribution line CL2 is a curve which is shifted in the minus direction from fitting curve FC by the standard deviation. The correction parameter analysis unit 39 counts the sampling points which are outside of standard distribution line CL1 and standard distribution line CL2 as exception points. The stability of the X-ray tube 13 can be measured based on how the standard distribution spreads. The spreading degree of the standard distribution can be calculated based on the difference between standard distribution line CL1 and standard distribution line CL2 at each point of time. If the standard distribution exceeds a threshold, it can be presumed that the operating condition of the X-ray tube 13 has varied. A change in the characteristics of the X-ray detection elements can be measured based on the change in the average, namely, the degree of curvature of the fitting curve. The degree of curvature of the fitting curve is calculated by time differential of the average at each time. If a change in the average exceeds a threshold, it can be presumed that the characteristics of the X-ray detection elements have varied. Based on a change in the number of exception points, the conditions of the environment maintaining apparatuses, such as an X-ray tube cooling apparatus and an X-ray detector heating apparatus, can be presumed. If the change in the number of exception points exceeds a threshold, it can be presumed that the condition of the environment maintaining apparatus has varied.

If it is determined in Step S4 that the statistical value exceeds a threshold (YES in Step S4), the system controller 53 causes the notification unit 41 to perform warning notification processing (Step S5). By use of the display apparatus 43 and the speaker 45, the notification unit 43 issues a warning that the statistical value has exceeded the threshold. For example, the notification unit 41 causes the display apparatus 43 to display a warning message such as "Check the apparatus," or causes the speaker 45 to issue a warning sound or a voice message that the apparatus must be checked. If a deteriorated member or component can be specified based on a combination of the type of a correction parameter and the type of a statistical value, the notification unit 41 may cause the display apparatus 43 or speaker 45 to indicate that the member or component in question should be checked.

If it is determined in Step S4 that the statistical value does not exceed the threshold (NO in Step S4), the system controller 53 causes the notification unit 41 to perform safety notification processing (Step S6). By use of the display apparatus 43 and the speaker 45, the notification unit 43 issues a message that the statistical value has not exceeded the threshold. For example, the notification unit 41 causes the display apparatus 43 to display a message such as "Apparatus is in good condition", or causes the speaker 45 to issue a voice message that the apparatus is in good condition or a sound indicating the good condition of the apparatus.

The processing in the collection parameter analysis aspect is performed as described above.

As described in the foregoing, the X-ray computed tomography apparatus of the present embodiment comprises: a correction section (a pre-processor 31, a reconstruction unit 33, and an image processor 35), a correction parameter storage 37, a correction parameter analysis unit 39, and a notification unit 41. The correction section corrects output data which is based on the electric signals supplied from the X-ray detector 15. The correction parameter storage 37 stores, in time series, correction parameters relating to the corrections made by the correction section. The correction parameter analysis unit 39 determines whether or not a statistical value of the correction parameters stored in the parameter storage 37 in time series exceeds a threshold. If the statistical value exceeds the threshold, a warning is issued.

The function of calculating or measuring correction parameters is incorporated in the normally-used CT scan algorithm. Therefore, the correction parameters can be accumulated in the correction parameter storage 37 during an ordinary CT scan, with no need to modify to the X-ray computed tomography apparatus. The correction parameters sensitively reflect the conditions of the members or components in each CT scan. By performing dynamic statistical analysis for the time-series correction parameters accumulated in the correction parameter storage 37, the correction parameter analysis unit 39 enables the user to know a symptom of the malfunction or deterioration of a member or component before the apparatus becomes unusable due to the malfunction or deterioration. Confirming the symptom of the malfunction or deterioration, the user can consider when the apparatus should be maintained, adjust the CT value parameters, or prepare a replacement part or component used at the time of the maintenance, before the apparatus becomes unusable in practice.

The correction parameter analysis processing according to the embodiment does not require an operation hard to perform or professional knowledge. It is not necessary to ask a service technician to perform the correction parameter analysis processing. The correction parameter analysis processing can be performed by the medical staff of the facility where the X-ray computed tomography apparatus is installed. In the analysis processing, the correction parameters accumulated in the correction parameter storage 37 are subjected to statistical analysis, and a CT scan need not be executed anew. The user can execute the correction parameter analysis processing with no considerable burden related to time or labor.

As described above, the present embodiment provides an X-ray computed tomography apparatus that enables the operating condition to be checked at any time desired.

(Modification)

The X-ray computed tomography apparatus described above is merely an example, and the embodiment is not limited to the structure described above. For example, part of the above X-ray computed tomography apparatus may be installed in another information processing apparatus. In the following, reference will be made to an information processing apparatus according to a modification. In the description below, the same reference numerals and symbols as used in connection with the aforementioned embodiment will be used to denote corresponding or functionally-equivalent components, and a description of such components will be repeated, only when necessary.

Figure 5:
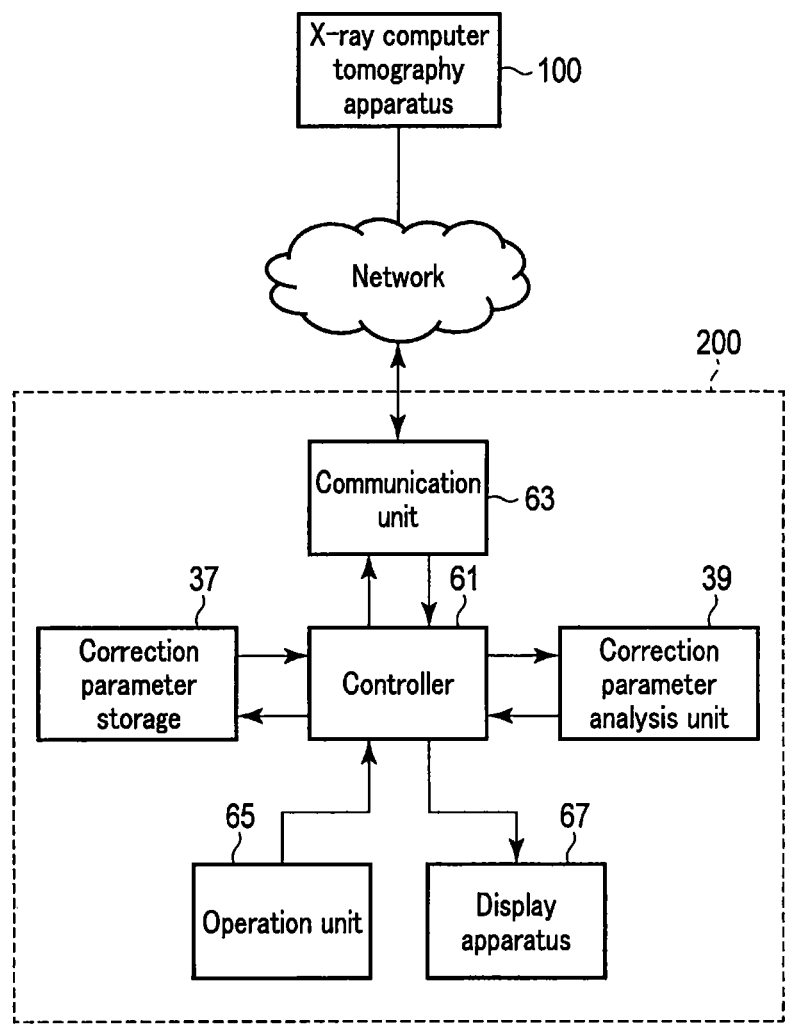
FIG. 5 is a diagram illustrating an information processing apparatus according to a modification.

FIG. 5 is a diagram illustrating an information processing apparatus 200 according to a modification. As shown in FIG. 5, the information processing apparatus 200 is connected to an X-ray computed tomography apparatus 100 by way of a network in such a manner that communications are enabled. The X-ray computed tomography apparatus 100 comprises a gantry 10 and a console 30. The console 30 comprises structural elements other than those used for the correction parameter analysis. To be more specific, the console 30 of the modification comprises a pre-processor 31, a reconstruction unit 33, an image processor 35, a notification unit 41, a display apparatus 43, a speaker 45, an operation unit 47, a main storage 49, a scan controller 51 and a system controller 53.

The information processor 200 comprises a controller 61 (a major element), a correction parameter storage 37, a correction parameter analysis unit 39, a communication unit 63, an operation unit 65, and a display apparatus 67.

The communication unit 63 performs information communications with the X-ray computed tomography apparatus by way of the network. The display apparatus 67 displays information on a display. The operation unit 65 is supplied with various types of instructions and information which the user enters from an input device.

By virtue of the above structure or configuration, the communication unit 63 receives correction parameters which are used in the X-ray computed tomography apparatus 100 for a series of correction processes related to reconstruction image generation processing. It should be noted here that the reconstruction image generation processing includes various type of processing, beginning with pre-processing to raw data, followed by image reconstruction processing, and ending with image processing to a reconstruction image. The received correction parameters are stored in the correction parameter storage 37 in time series. As described above, the correction parameter analysis unit 39 determines whether or not the apparatus is in an abnormal state based on a temporal change in the correction parameters supplied from the X-ray computed tomography apparatus 100. The correction unit 63 transmits to the X-ray computed tomography apparatus 100 a signal representing the result of the determination made by the correction parameter analysis unit 39. To be more specific, the correction unit 63 transmits a normality signal if the correction parameter analysis unit 39 determines that the apparatus is not in an abnormal state, and transmits an abnormality signal if the correction parameter analysis unit 39 determines that the apparatus is in an abnormal state. The notification unit 41 of the X-ray computed tomography apparatus 100 issues a notification result based on the analysis of the correction parameter analysis unit 39. To be more specific, the notification unit 41 issues a notice that the apparatus is not in an abnormal state if the information processing apparatus 200 transmits a normality signal, and issues an abnormality signal if the information processing apparatus transmits an abnormality signal.

The X-ray computed tomography apparatus 100 may be configured to transmit a correction parameter to the information processing apparatus 200 each time the correction parameter is generated. In this case, the correction parameter storage 37 may store the correction parameter from the X-ray computed tomography apparatus 100 by using, for example, an HDD having comparatively large storage capacity. The X-ray computed tomography apparatus 100 may be configured to transmit a correction parameter to the information processing apparatus 200 in response to a request signal output from the information processing apparatus 200. In this case, the correction parameter storage 37 may store a correction parameter from the X-ray computed tomography apparatus 100 by using a memory having comparatively small storage capacity.

As described above, the modification provides an X-ray computed tomography apparatus that enables the operating condition to be checked at any time desired.

The embodiment and modification described above are presented merely as examples, and are not intended to limit the scope of an invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
    an X-ray tube which generates X-rays;
    an X-ray detector which detects X-rays generated from the X-ray tube;
    processing circuitry configured to generate a reconstruction image based on output data in accordance with an electric signal from the X-ray detector; and
    a memory which stores correction parameters in time series, the correction parameters being used for correction by which noise or an artifact is reduced in processing performed by the processing circuitry, wherein the processing circuitry is further configured to
    determine whether the apparatus is in an abnormal state based on a temporal change in the correction parameters stored in the memory, and
    issue a notification of occurrence of an abnormal condition when the processing circuitry determines that the apparatus is in the abnormal state.

2. The apparatus according to claim 1, wherein the processing circuitry is further configured to
    determine whether or not the apparatus is in the abnormal state by checking whether a statistical value of the correction parameters stored in the memory in time series exceeds a threshold, and
    issue occurrence of the abnormal condition when the statistical value exceeds the threshold.

3. The apparatus according to claim 2, wherein the statistical value checked by the processing circuitry comprises at least one of an average, a change in the average, a standard deviation, a change in the standard deviation, a dispersion, a change in the dispersion, a standard distribution, a change in the standard distribution, a number of exception points, and a change in the number of exception points.

4. The apparatus according to claim 1, wherein the processing circuitry is further configured to
    generate digital raw data corresponding to electric signals from the X-ray detector, and
    generate image data from the raw data by performing image reconstruction processing to the raw data, and
    the correction parameters include at least one of a correction parameter used for correction of the raw data, a correction parameter used for correction incorporated in the image reconstruction processing, and a correction parameter used for correction of the image data.

5. The apparatus according to claim 1, wherein the correction parameters stored in the memory include a parameter representing a number of iterations of correction processing.

6. The apparatus according to claim 4, wherein the correction of the raw data is one of X-ray intensity correction, offset correction, beam hardening correction and body motion correction.

7. The apparatus according to claim 6, wherein a correction parameter used for the correction of the X-ray intensity is one of an X-ray output value, a tube voltage value, and a tube current value of a reference detector.

8. The apparatus according to claim 6, wherein a correction parameter used for the offset correction is one of a detector output value and a gain value corresponding to an X-ray detection element.

9. The apparatus according to claim 4, wherein the correction incorporated in the image reconstruction processing and the correction to the image data comprise at least one of ring correction and noise reducing processing.

10. The apparatus according to claim 9, wherein processing strength of the ring correction or a number of iterations is used as a correction parameter related to the ring correction.

11. The apparatus according to claim 10, wherein the processing strength is a coefficient of a function for reducing ring components.

12. The apparatus according to claim 10, wherein the number of iterations is a number of times the ring correction is repeated.

13. The apparatus according to claim 9, wherein smoothing strength in smoothing processing is used as a correction parameter related to the noise reduction processing.

14. An information processing apparatus connected to an X-ray computed tomography apparatus by way of a network, comprising:
    processing circuitry configured to determine whether or not an abnormal condition occurs based on a temporal change in correction parameters, the correction parameters being used in correction which is executed when the X-ray computed tomography apparatus generates a reconstruction image; and
    a transmitter configured to transmit a notification signal indicating occurrence of an abnormal condition to the X-ray computed tomography apparatus when the processing circuitry determines that the abnormal condition occurs.

* * * * *